United States Patent
Schabbach et al.

(10) Patent No.: US 10,046,111 B2
(45) Date of Patent: Aug. 14, 2018

(54) NEEDLE INSERTION AND RETRACTION ARRANGMENT WITH MANUALLY TRIGGERED, SPRING-LOADED DRIVE MECHANISM

(71) Applicant: Sanofi-Aventis Deutschland GMBH, Frankfurt am Main (DE)

(72) Inventors: Michael Schabbach, Frankfurt am Main (DE); Meinolf Werner, Worms (DE); Olaf Zeckai, Weinheim (DE); Philippe Nzike, Frankfurt am Main (DE)

(73) Assignee: Sanofi-Aventis Deutchland GMBH, Frankfurt am Main (DE)

( * ) Notice: Subject to any disclaimer, the term of this patent is extended or adjusted under 35 U.S.C. 154(b) by 301 days.

(21) Appl. No.: 14/916,664

(22) PCT Filed: Sep. 2, 2014

(86) PCT No.: PCT/EP2014/068595
§ 371 (c)(1),
(2) Date: Mar. 4, 2016

(87) PCT Pub. No.: WO2015/032741
PCT Pub. Date: Mar. 12, 2015

(65) Prior Publication Data
US 2016/0213837 A1   Jul. 28, 2016

(30) Foreign Application Priority Data

Sep. 5, 2013 (EP) .................................... 13183150

(51) Int. Cl.
*A61M 5/158* (2006.01)
*A61B 5/15* (2006.01)
(Continued)

(52) U.S. Cl.
CPC ........ *A61M 5/158* (2013.01); *A61M 5/14244* (2013.01); *A61B 5/15003* (2013.01);
(Continued)

(58) Field of Classification Search
CPC .... A61M 5/20; A61M 5/158; A61M 5/14244; A61M 5/14248; A61M 5/3287;
(Continued)

(56) References Cited

U.S. PATENT DOCUMENTS 4,658,744 A * 4/1987 Takauchi ............... D05B 69/24
112/448
5,306,281 A * 4/1994 Beurrier ............. A61B 17/0491
112/116

(Continued)

FOREIGN PATENT DOCUMENTS

| EP | 2586475 | 5/2013 |
|---|---|---|
| WO | WO2008/098246 | 8/2008 |
| WO | WO2009/010399 | 1/2009 |

OTHER PUBLICATIONS

International Search Report and Written Opinion in International Application No. PCT/EP2014/068595, dated Oct. 29, 2014, 11 pages.

(Continued)

*Primary Examiner* — Nathan R Price
*Assistant Examiner* — Dung Ulsh
(74) *Attorney, Agent, or Firm* — Fish & Richardson P.C.

(57) ABSTRACT

Disclosed is a needle insertion arrangement (1) with a drive mechanism (9) comprising: a belt (15) frictionally engaging a first roller (10) and a needle retainer (7) with an injection needle (2) fixed to the belt, the first roller being rotatably arranged about an axis (A), a second roller (11) also rotatably arranged about the axis (A), a first spring (13) rotatably biasing the first roller against the second roller, a second
(Continued)

spring (14) rotatably biasing the second roller against an arrester (12), the first and the second roller being connected via an internal protrusion (10.2) and arcuate slot (11.2), the two springs (13, 14) biasing the rollers (10, 11) from respective first to respective second angular positions ($AP1_1$, $AP1_2$, $AP2_1$, $AP2_2$), and a trigger mechanism (17,20) releasably locking the first and second rollers (10, 11) such that upon pivoting the trigger button (20) in one direction, the first roller drives the belt in one direction to linearly transport the needle retainer towards an extended position, and upon pivoting the trigger button in the other direction, the first roller drives the belt back to retract the needle retainer.

20 Claims, 10 Drawing Sheets (51) Int. Cl.
 *A61M 5/32* (2006.01)
 *A61M 5/142* (2006.01)

(52) U.S. Cl.
 CPC ...... *A61B 5/15019* (2013.01); *A61M 5/14248* (2013.01); *A61M 5/3287* (2013.01); *A61M 2005/14256* (2013.01); *A61M 2005/1581* (2013.01); *A61M 2005/1583* (2013.01); *A61M 2005/1585* (2013.01)

(58) Field of Classification Search
 CPC .. A61M 2005/206; A61M 2005/14256; A61M 2005/1584; A61M 2005/1583; A61M 2005/1585; A61M 37/0076–37/0084; A61M 5/14232; A61B 1/01; A61B 5/15019; A61B 5/15003
 See application file for complete search history.

(56) References Cited

U.S. PATENT DOCUMENTS

| | | | | |
|---|---|---|---|---|
| 5,339,757 A * | 8/1994 | Nakano | ............... | D05B 55/14 112/163 |
| 5,816,512 A * | 10/1998 | Nakashima | ............ | D05B 59/00 112/279 |
| 5,860,992 A * | 1/1999 | Daniel | ............... | A61B 17/0469 606/139 |
| 6,044,780 A * | 4/2000 | Kastrup | ............... | D05B 3/08 112/66 |
| 2006/0090681 A1* | 5/2006 | Ota | ............... | D05B 19/16 112/459 |
| 2007/0062427 A1* | 3/2007 | Kondo | ............ | D05B 37/04 112/68 |
| 2007/0107470 A1* | 5/2007 | Tajima | ............... | D05B 55/14 66/116 |
| 2008/0269687 A1* | 10/2008 | Chong | ............... | A61L 15/58 604/180 |
| 2008/0319414 A1 | 12/2008 | Yodfat et al. | | |
| 2009/0007830 A1* | 1/2009 | Sakuma | ............... | D05B 1/02 112/475.17 |
| 2009/0099521 A1* | 4/2009 | Gravesen | ............ | A61M 5/14248 604/136 |
| 2009/0129831 A1* | 5/2009 | Sakashita | ............ | G03G 15/1675 399/309 |
| 2010/0163351 A1* | 7/2010 | Sakashita | ................ | B60T 7/107 188/182 |
| 2010/0292651 A1* | 11/2010 | Yodfat | ................ | A61M 5/1413 604/189 |
| 2011/0130782 A1 | 6/2011 | Kan et al. | | |
| 2011/0178461 A1* | 7/2011 | Chong | ............. | A61M 5/14248 604/151 |
| 2012/0109062 A1* | 5/2012 | Lanigan | ............... | A61B 5/1427 604/164.12 |
| 2012/0316019 A1* | 12/2012 | Ward | ................... | F16H 7/1218 474/135 |
| 2013/0060233 A1* | 3/2013 | O'Connor | ............ | A61M 5/158 604/506 |
| 2014/0031793 A1* | 1/2014 | Constantineau | .. | A61M 5/14248 604/510 |
| 2014/0296825 A1* | 10/2014 | Lemaire | ................ | A61M 5/158 604/506 |
| 2016/0030292 A1* | 2/2016 | Hyun | .................. | A61J 15/0076 604/516 |
| 2016/0184512 A1* | 6/2016 | Marbet | ................. | A61M 5/158 604/156 |
| 2016/0354553 A1* | 12/2016 | Anderson | ........... | A61M 5/3298 |
| 2017/0128664 A1* | 5/2017 | Diianni | ............... | A61M 5/1452 |
| 2017/0143900 A1* | 5/2017 | Rioux | ............... | A61M 5/14216 |
| 2017/0182303 A1* | 6/2017 | Tallarida | ........... | A61M 39/0208 |
| 2017/0258489 A1* | 9/2017 | Galili | ................. | A61B 17/3403 |
| 2017/0281878 A1* | 10/2017 | Wickham | ............ | A61M 5/3245 |
| 2017/0312488 A1* | 11/2017 | Chowdhury | ...... | A61M 37/0015 |

OTHER PUBLICATIONS

International Preliminary Report on Patentability in International Application No. PCT/EP2014/068595, dated Mar. 8, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

NEEDLE INSERTION AND RETRACTION ARRANGMENT WITH MANUALLY TRIGGERED, SPRING-LOADED DRIVE MECHANISM

CROSS-REFERENCE TO RELATED APPLICATIONS

This application is a U.S. national stage application under 35 USC § 371 of International Application No. PCT/EP2014/068595, filed on Sep. 2, 2014, which claims priority to European Patent Application No. 13183150.5, filed on Sep. 5, 2013, the entire contents of which are incorporated herein by reference.

TECHNICAL FIELD

The invention relates to a drive mechanism for a needle insertion arrangement.

BACKGROUND OF THE INVENTION

Administering an injection is a process which presents a number of risks and challenges for users and healthcare professionals, both mental and physical. During manual insertion of an injection needle into an injection site, e.g. the skin of a patient, it may be difficult to avoid tilting and bending of the needle and the insertion may be slow thus causing pain.

There remains a need for an improved drive mechanism for a needle insertion arrangement.

SUMMARY OF THE INVENTION

Aspects of the present invention can provide an improved drive mechanism for a needle insertion arrangement.

The aspects can be implemented by a drive mechanism for a needle insertion arrangement according to claim 1.

Exemplary embodiments of the invention are given in the dependent claims.

According to the invention a drive mechanism for a needle insertion arrangement comprises:
  at least one rotatable roller,
  at least one spring adapted to bias the roller from a first angular position towards a second angular position,
  a belt adapted to frictionally engage the roller and adapted to be fixed to a needle retainer, and
  a trigger mechanism adapted to releasably lock the roller in the first angular position.

In an exemplary embodiment the drive mechanism further comprises a needle retainer adapted to retain an injection needle, the needle retainer arranged to be moved between a retracted position and an extended position.

In an exemplary embodiment the drive mechanism further comprises:
  a first roller adapted to frictionally engage the belt and rotatably arranged about an axis,
  a second roller rotatably arranged about the axis,
  a first spring adapted to rotatably bias the first roller against the second roller,
  a second spring adapted to rotatably bias the second roller against an arrester.

In an exemplary embodiment the spring is arranged as a torsion spring.

In an exemplary embodiment the drive mechanism further comprises an arrangement for limiting rotation of the first roller relative the second roller.

In an exemplary embodiment one of the first roller and the second roller comprises an internal protrusion adapted engage an arcuate slot within the other one of the first roller and the second roller.

In an exemplary embodiment the first roller is adapted to maintain the needle retainer in a retracted position when the first roller is in the first angular position and to move the needle retainer from the retracted position into an extended position when the first roller is rotated from the first angular position in a second rotational direction to a second angular position.

In an exemplary embodiment the second roller is adapted to rotate the first roller from the second angular position in a first rotational direction to the first angular position through the arrangement for limiting rotation when the second roller is rotated from the first angular position in the first rotational direction to the second angular position thereby moving the needle retainer from the extended position into the retracted position.

In an exemplary embodiment the drive mechanism further comprises two deflection pulleys, wherein the belt is guided over the deflection pulleys, wherein the belt is fixed to the needle retainer between the two deflection pulleys.

In an exemplary embodiment the trigger mechanism comprises:
  at least one external recess arranged in the roller,
  at least one trigger hook with a protrusion adapted to engage the at least one external recess for locking the roller in the first angular position.

In an exemplary embodiment the drive mechanism further comprises:
  a trigger button,
  an engagement surface on the trigger hook adapted to be engaged by the trigger button upon operation.

In an exemplary embodiment the at least one trigger hook and/or the trigger button are/is adapted to be tilted about a respective axis.

In an exemplary embodiment the trigger button is adapted to engage one of the trigger hooks thereby disengaging the respective protrusion from the external recess, when the trigger button is tilted in one of the rotational directions, wherein the trigger button is adapted to engage the other one of the trigger hooks thereby disengaging the respective protrusion from the external recess, when the trigger button is tilted in the other one of the rotational directions.

The drive mechanism may be applied in an insertion arrangement for moving an injection needle between a retracted position and an extended position, comprising a disposable unit, comprising a needle base, to which the needle is fixed, and the drive mechanism, wherein the needle retainer is adapted to retain the needle base.

The insertion arrangement has only limited space requirements thus allowing for low profile injection devices with a high wearing comfort. The insertion arrangement achieves high speed needle movements and exact needle guidance thus reducing pain for the patients when inserting and retracting the needle and increasing consumer acceptance and satisfaction. The low part count of the insertion arrangement allows for an increased mechanical robustness and low manufacturing costs. The insertion arrangement is a fault-tolerant system. In the insertion arrangement a single button is used for triggering both needle insertion and needle retraction.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
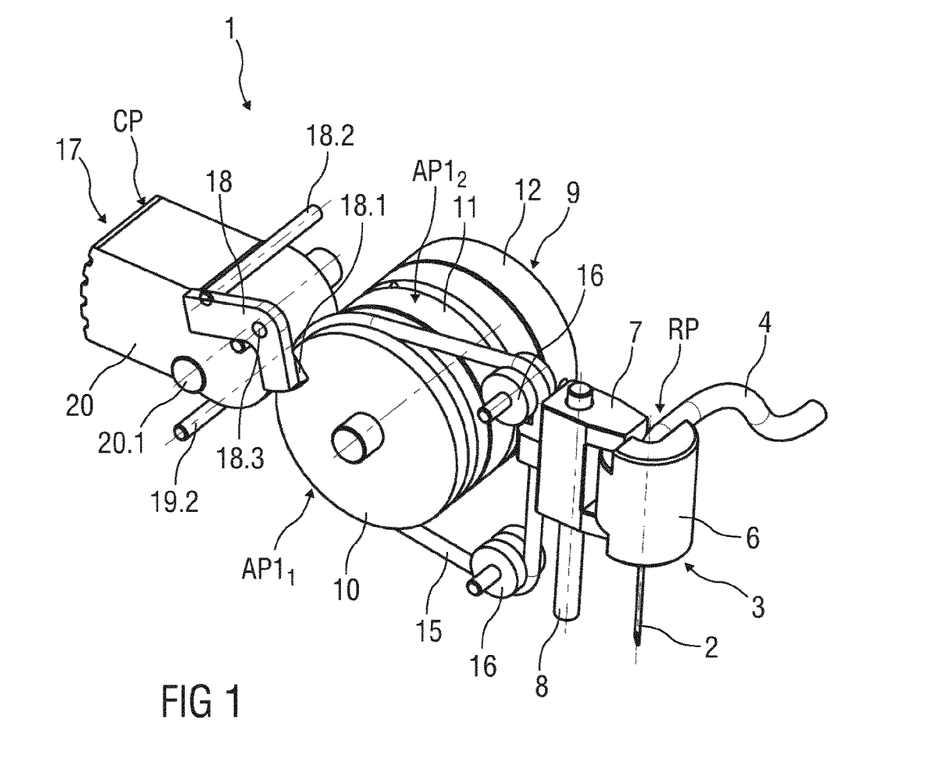
FIG. 1 is a schematic perspective view of an exemplary embodiment of an insertion arrangement for inserting an injection needle into an injection site, the insertion arrangement comprising a drive mechanism.
Figure 2:
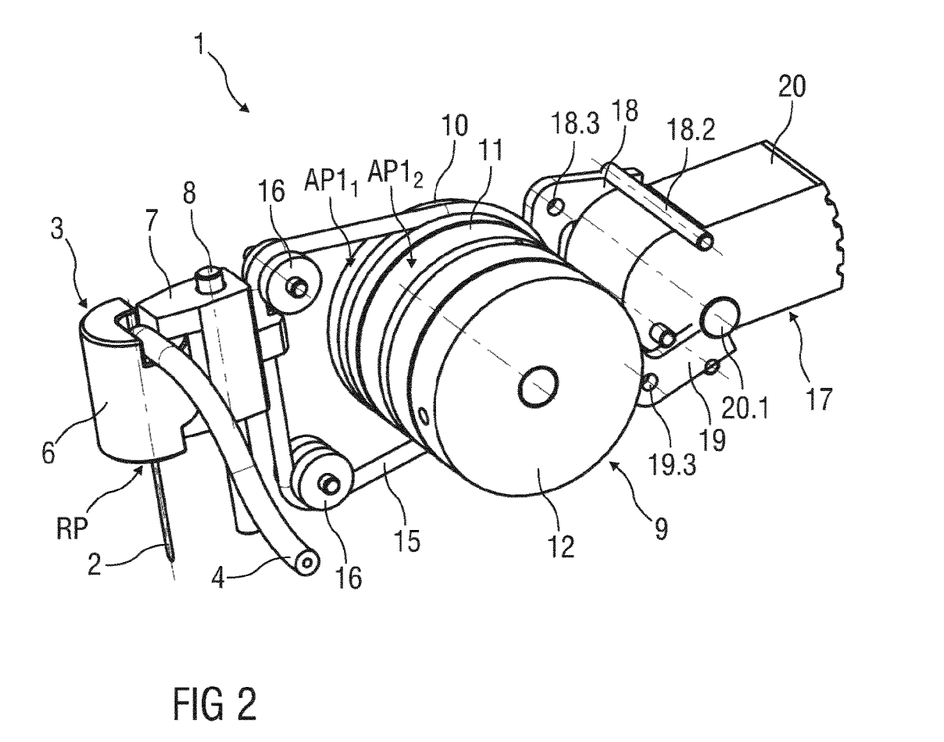
FIG. 2 is another schematic perspective view of the insertion arrangement.
Figure 3A:
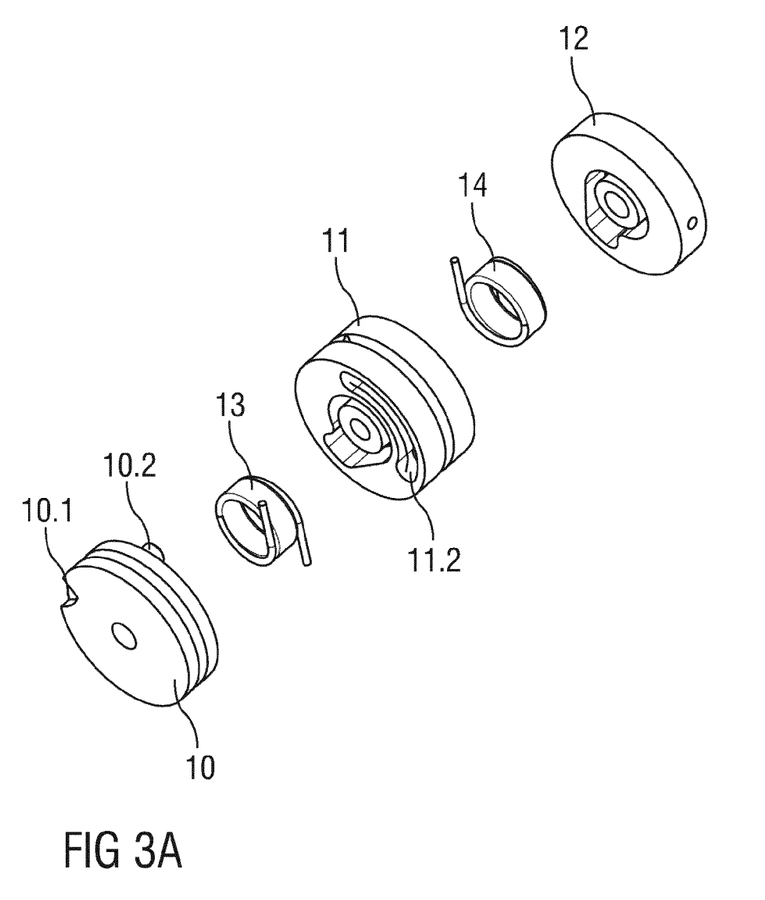
FIGS. 3A to 3D are different schematic exploded perspective views of rollers of the drive mechanism.
Figure 3B:
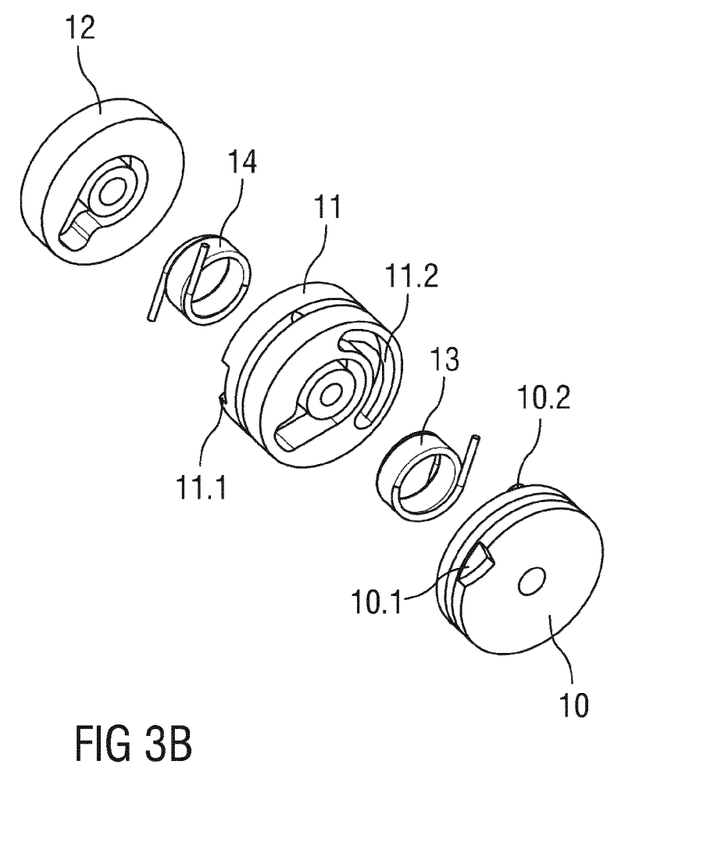
Figure 3C:
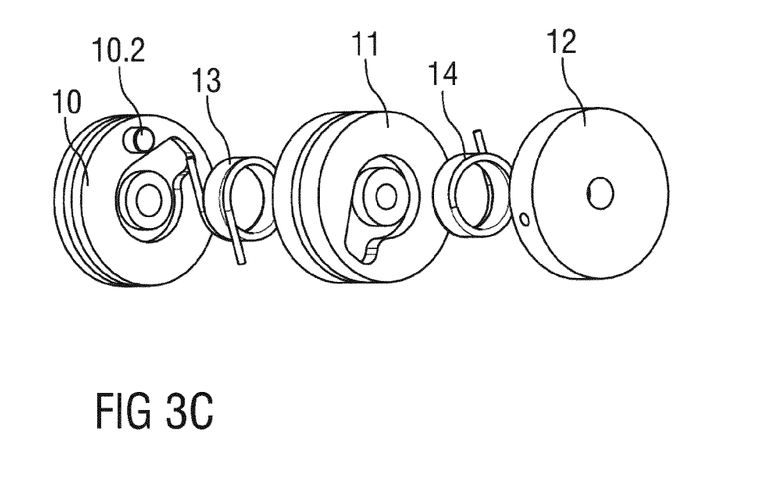
Figure 3D:
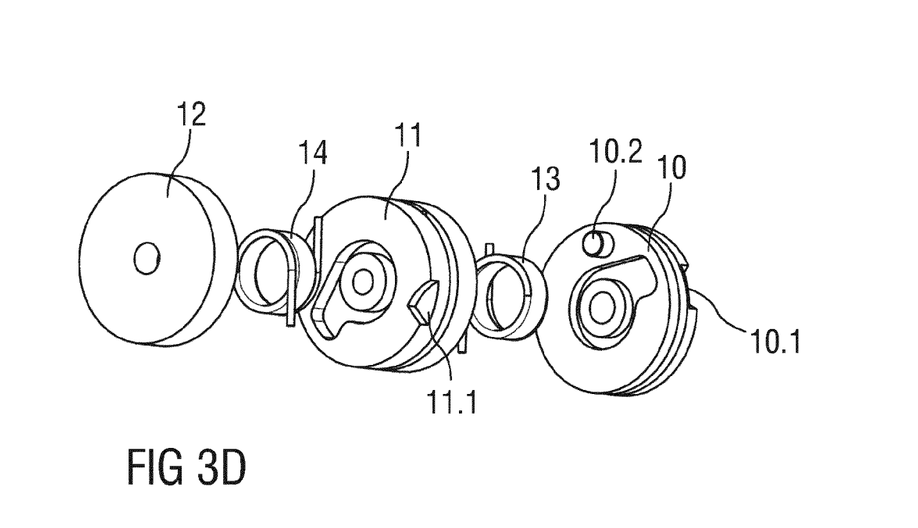

FIG. 1 is a schematic perspective view of an exemplary embodiment of an insertion arrangement 1 for automatically or semi-automatically inserting an injection needle 2 into an injection site. FIG. 2 is another related perspective view. The arrangement 1 may be applied in medicament pumps, e.g. insulin pumps which may be permanently worn on the body.

The injection needle 2 is part of a disposable unit 3, further comprising a tube 4 for establishing a fluid communication of the needle 2 with a drug container (not illustrated) and comprising a needle base 6, to which the injection needle 2 may be fixed for mechanically connecting the needle 2 to a drive mechanism 9 of an injection unit (not illustrated). The needle base 6 is inserted in a forked needle retainer 7 which is arranged to be moved up and down in a linear guide 8. This linear movement corresponds to insertion of the needle 2 into the injection site, e.g. subcutaneous body tissue and removal from the injection site, respectively.

A drive mechanism 9 for the needle 2 comprises three rollers 10, 11, 12 arranged on a common axis A. FIGS. 3A to 3D are schematic exploded perspective views of the rollers 10, 11, 12. A first roller 10 is engaged through a first torsion spring 13 to a second roller 11 which is in turn engaged through a second torsion spring 14 to a third roller 12. The third roller 12 is rotationally fixed and serves as an arrester for the second torsion spring 14. In an exemplary embodiment the third roller 12 could be replaced by a different arrester with an arbitrary shape. The first roller 10 and the second roller 11 are rotatably arranged about the axis A. The first roller 10 and the second roller 11 comprise respective external recesses 10.1, 11.1 which may be used for rotationally locking the first roller 10 and/or the second roller 11 in respective first angular positions. The first roller 10 furthermore comprises an internal protrusion 10.2 adapted to be engaged in an arcuate slot 11.2 within the second roller 11 for limiting the rotation of the first roller 10 relative the second roller 11. In an alternative embodiment the internal protrusion could be arranged on the second roller 11 and the arcuate slot in the first roller 10. Furthermore, the internal protrusion 10.2 and the arcuate slot 11.2 could be replaced by a different arrangement for limiting the rotation of the first roller 10 relative the second roller 11.

Referring again to FIGS. 1 and 2, the first roller 10 is frictionally engaged by a belt 15 which is guided over two deflection pulleys 16. Between the two deflection pulleys 16 the belt is fixed to the needle retainer 7. If the first roller 10 is rotated, the belt 15 is advanced thereby moving the needle retainer 7 and hence the needle 2. A direction of this movement depends on a rotational direction of the first roller 10. A trigger mechanism 17 is arranged to engage the external recess 10.1 of the first roller 10 and lock it in the first angular position $AP1_1$ and/or to engage the external recess 11.1 of the second roller 11 and lock it in the first angular position $AP1_2$. In an exemplary embodiment the trigger mechanism 17 comprises a first trigger hook 18 with a protrusion 18.1 for engaging the external recess 10.1 of the first roller 10, a second trigger hook 19 with a protrusion 19.1 for engaging the external recess 11.1 of the second roller 11 and a trigger button 20 for operating the trigger hooks 18, 19. Each trigger hook 18, 19 further comprises an engagement surface 18.2, 18.3, e.g. in the shape of a spring wire, adapted to be engaged by the trigger button 20 upon operation. In the illustrated exemplary embodiment the trigger hooks 18, 19 and the trigger button 20 are arranged to be tilted about respective axes 18.3, 19.3, 20.1. When the trigger button 20 is tilted in one rotational direction it engages one of the trigger hooks 18, 19 thereby disengaging the respective protrusion 18.1, 19.1 from the external recess 10.1, 11.1. When the trigger button 20 is tilted in another, opposite, rotational direction it engages the other one of the trigger hooks 19, 18 thereby disengaging the respective protrusion 19.1, 18.1 from the external recess 11.1, 10.1. A spring (not illustrated) may be arranged for biasing the trigger button towards a central position CP where neither the first trigger hook 18 nor the second trigger hook 19 is engaged.

In an alternative embodiment the trigger mechanism 17 could be arranged to linearly move a protrusion in and out of the external recess 10.1.

The torsion springs 13, 14 serve for providing the energy required to move the needle retainer 7. In order to prepare the drive mechanism 9 for an injection the second roller 11 is rotated thus charging the torsion springs 13, 14. A cocking arrangement (not illustrated) may be arranged to facilitate rotating the second roller 11.

Figure 4:
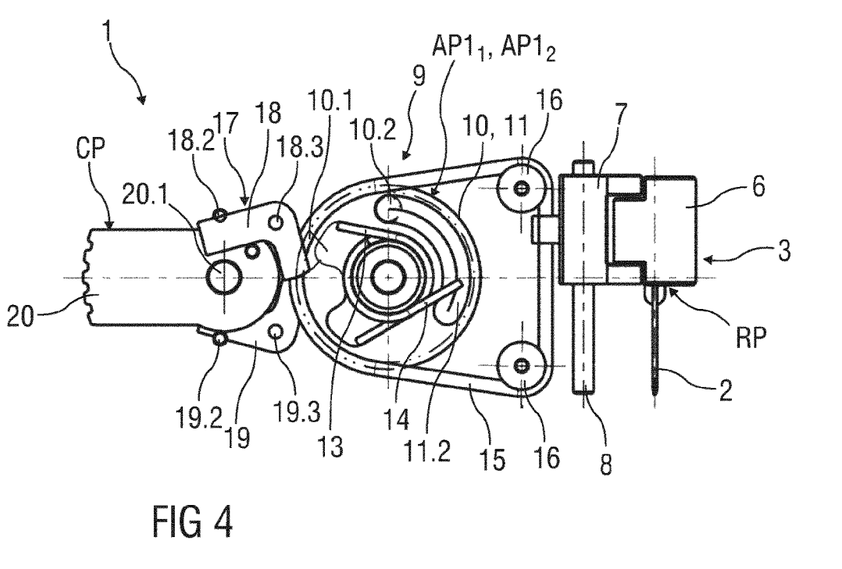
FIG. 4 is a schematic side view of the insertion arrangement in an initial position with a needle in a retracted position.

A sequence of operation of the insertion arrangement 1 is as follows:

FIG. 4 is a schematic side view of the insertion arrangement 1 in an initial position. The disposable unit 3 with the needle base 6, the needle 2 and the tube 4 has been inserted in the forked needle retainer 7. The first roller 10 is in the first angular position $AP1_1$ thus maintaining the needle retainer 7 in a retracted position RP through the belt 15. The two torsion springs 13, 14 are cocked. The protrusions 18.1, 19.1 of the trigger mechanism 17 engage the external recesses 10.1, 11.1 of the first roller 10 and the second roller 11 thus preventing the torsion springs 13, 14 from relaxing and rotating the first and/or second roller 10, 11. The trigger button 20 is in the central position CP neither engaging the first trigger hook 18 nor the second trigger hook 19.

Figure 5:
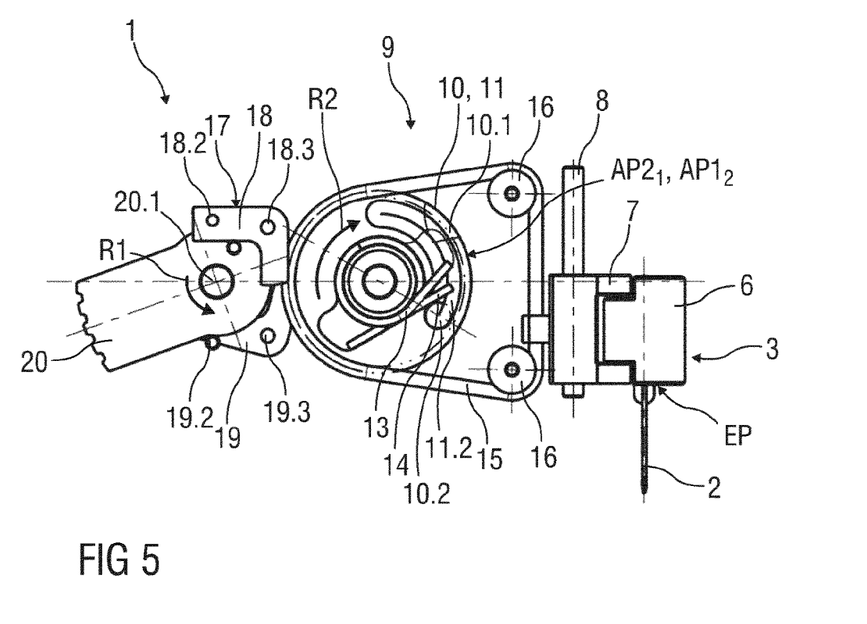
FIG. 5 is a schematic side view of the insertion arrangement during operation of a trigger button.

FIG. 5 is a schematic side view of the insertion arrangement 1 during operation of the trigger button 20. Starting from the central position CP the trigger button 20 has been tilted about its axis 20.1 in the first rotational direction R1 thus displacing the engagement surface 18.1 of the first trigger hook 18 which is hence tilted about its axis 18.3 in the second rotational direction R2. Thus, the protrusion 18.1 of the first trigger hook 18 disengages the external recess 10.1 of the first roller 10 allowing the first torsion spring 13 to relax and rotate the first roller 10 from the first angular position $AP1_1$ in the second rotational direction R2 to a second angular position $AP2_1$, which may for example be 120° offset from the first angular position $AP1_1$. In the second angular position $AP2_1$ the internal protrusion 10.2 of the first roller 10 abuts against an end of the arcuate slot 11.2 of the second roller 11, which is in the first angular position $AP1_2$. The rotation of the first roller 10 conveys the belt 15 and hence moves the needle retainer 7 with the needle 2 from the retracted position RP into the extended position EP in order to rapidly insert the needle 2 into an injection site. A needle insertion depth, e.g. in the subcutaneous body tissue, may be determined by the needle retainer 7 abutting a stop (not illustrated) on the linear guide 8 or by the needle retainer 7 abutting one of the deflection pulleys 16.

Figure 6:
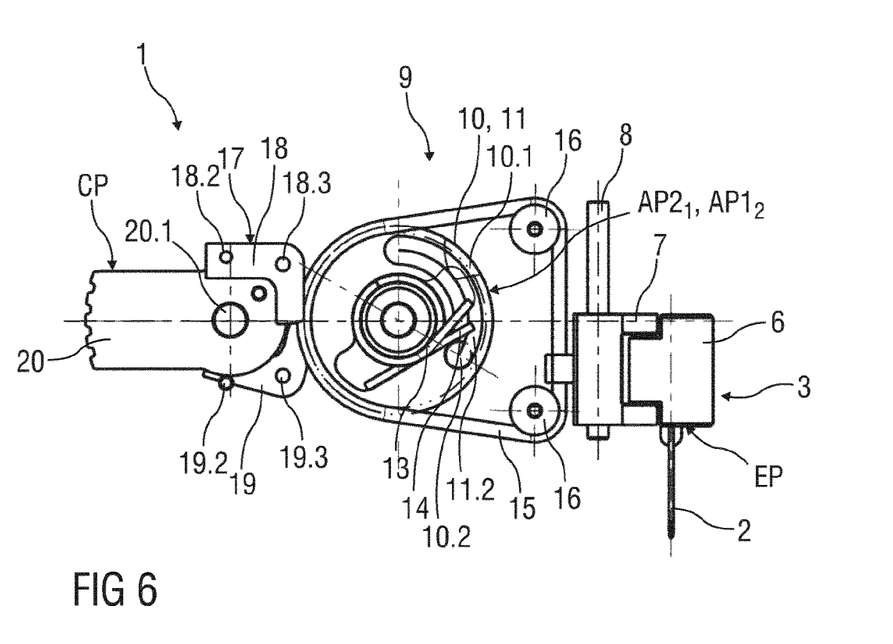
FIG. 6 is a schematic side view of the insertion arrangement with the needle in an extended position and after release of the trigger button.

FIG. 6 is a schematic side view of the insertion arrangement 1 with the needle 2 in the extended position EP and after release of the trigger button 20. The trigger button 20 has returned to its central position CP. The first trigger hook 18 cannot return to its prior position as the external recess 10.1 of the first roller 10 is no longer aligned with the protrusion 18.1. The second trigger hook 19 remains engaged to the second roller 11 thus preventing the second torsion spring 14 from relaxing and rotating the second roller 11.

Figure 7:
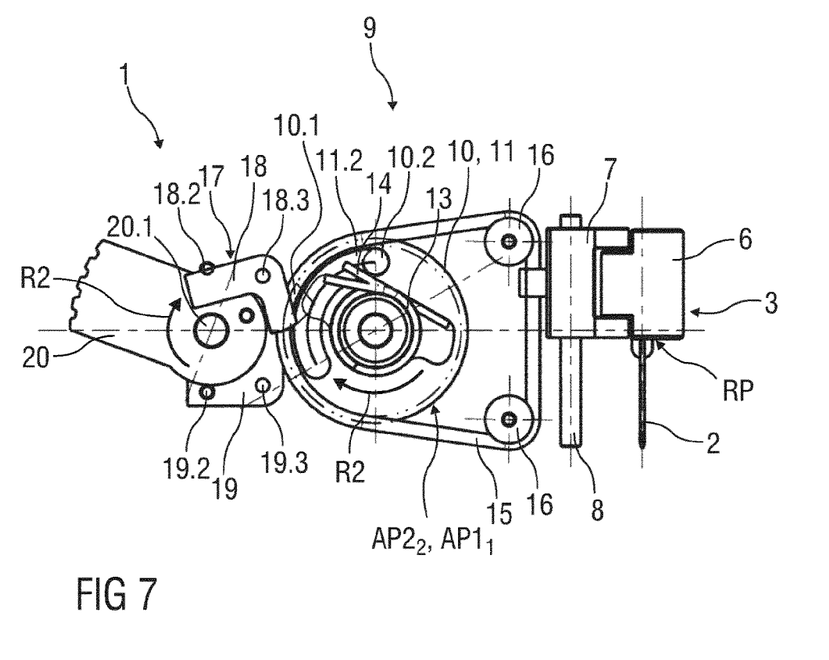
FIG. 7 is a schematic side view of the insertion arrangement with the needle in the extended position and during operation of the trigger button.

FIG. 7 is a schematic side view of the insertion arrangement 1 with the needle 2 in the extended position EP and during another operation of the trigger button 20. Starting from the central position CP the trigger button 20 has been tilted about its axis 20.1 in the second rotational direction R2 thus displacing the engagement surface 19.1 of the second trigger hook 19 which is hence tilted about its axis 19.3 in the first rotational direction R1. Thus, the protrusion 19.1 of the second trigger hook 19 disengages the external recess 11.1 of the second roller 11 allowing the second torsion spring 14 to relax and rotate the second roller 11 from the first angular position $AP1_2$ in the first rotational direction R1 to a second angular position $AP2_2$, which may for example be 120° offset from the first angular position $AP1_2$. Due to the internal protrusion 10.2 of the first roller 10 being abutted against an end of the arcuate slot 11.2 of the second roller 11 the rotation of the second roller 11 causes rotation of the first roller 10 from its second angular position $AP2_1$ in the first rotational direction R1 to the first angular position $AP1_1$. This rotation conveys the belt 15 and hence moves the needle retainer 7 with the needle 2 from the extended position EP into the retracted position RP in order to retract the needle 2 from the injection site. The rotation of the first roller 10 back into the first angular position $AP1_1$ also aligns the external recess 10.1 of the first roller 10 with the protrusion 18.1 of the first trigger hook 18 allowing the protrusion 18.1 to enter the external recess 10.1 and lock the first roller 10 in position.

Figure 8:
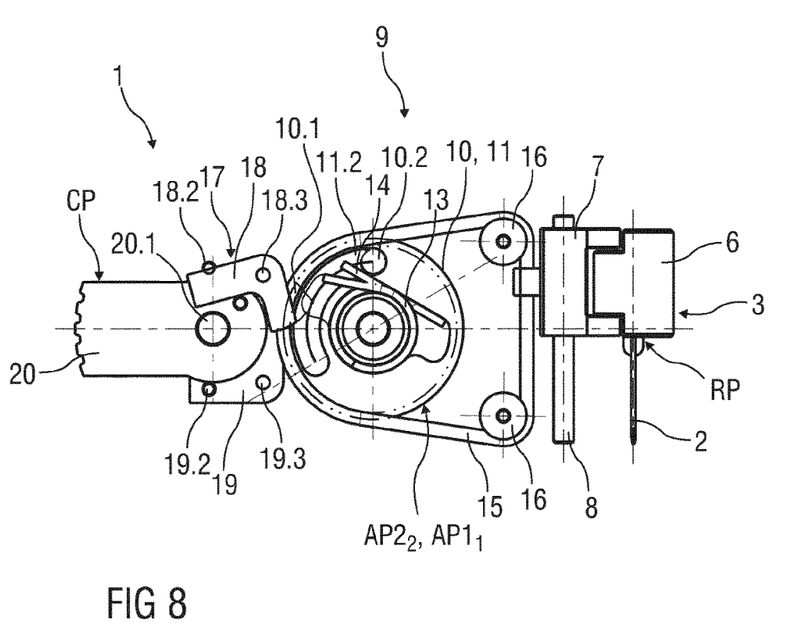
FIG. 8 is a schematic side view of the insertion arrangement with the needle in the retracted position and after release of the trigger button.

FIG. 8 is a schematic side view of the insertion arrangement 1 with the needle 2 in the retracted position RP and after release of the trigger button 20. The trigger button 20 has returned to its central position CP. The first second trigger hook 19 cannot return to its prior position as the external recess 11.1 of the second roller 11 is no longer aligned with the protrusion 19.1. The first trigger hook 18 remains engaged to the first roller 10 thus preventing the first torsion spring 13 from relaxing and rotating the first roller 10. Both torsion springs 13, 14 are relaxed.

Another injection can only be performed after the two torsion springs 13, 14 have been re-cocked by rotating the second roller 11 back into its first angular position $AP1_2$ in the second rotational direction R2. The second torsion spring 14 is cocked by the rotation as the third roller 12 is fixed in rotation against the axis A. The first torsion spring 13 is cocked by the rotation of the second roller 11 as it is engaged to the first roller 10 which is fixed in rotation by the protrusion 18.1 of the first trigger hook 18 engaging the external recess 10.1 of the first roller 10. The rotation of the second roller 11 back into the first angular position $AP1_2$ aligns the external recess 11.1 of the second roller 11 with the protrusion 19.1 of the second trigger hook 19 allowing the protrusion 19.1 to enter the external recess 11.1 and lock the second roller 11 in position. The insertion arrangement 1 would thus arrive in the initial state illustrated in FIG. 4.

A velocity profile of the needle 2 during movement between the retracted position RP and the extended position EP and vice versa can be modified by varying the diameter of the first roller 10. A fast movement of the needle 2 into the retracted position RP and the extended position EP is facilitated by the elasticity of the belt 15 and possible transmission-slip between the first roller 10 and the belt 15.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 insertion arrangement
2 injection needle
3 disposable unit
4 tube
5
6 needle base
7 needle retainer
8 linear guide
9 drive mechanism
10 first roller
10.1 external recess
10.2 internal protrusion
11 second roller
11.1 external recess
11.2 arcuate slot
12 third roller
13 first torsion spring
14 second torsion spring
15 belt
16 deflection pulley
17 trigger mechanism
18 first trigger hook
18.1 protrusion
18.2 engagement surface
18.3 axis
19 second trigger hook
19.1 protrusion
19.2 engagement surface
19.3 axis
20 trigger button
20.1 axis
A axis
$AP1_1$ first angular position
$AP2_1$ second angular position
$AP1_2$ first angular position
$AP2_2$ second angular position
CP central position
R1 first rotational direction
R2 second rotational direction

The invention claimed is:
1. A drive mechanism for a needle insertion arrangement, the drive mechanism comprising:
   a first roller adapted to frictionally engage a belt and rotatably arranged about an axis;
   a second roller rotatably arranged about the axis;

a first spring adapted to rotatably bias the first roller against the second roller from a first angular position towards a second angular position;

a second spring adapted to rotatably bias the second roller against an arrester from a third angular position towards a fourth angular position;

the belt adapted to frictionally engage the first roller and adapted to be fixed to a needle retainer; and a trigger mechanism adapted to releasably lock the first roller in the first angular position or the second roller in the third angular position.

2. The drive mechanism according to claim 1, comprising the needle retainer adapted to retain an injection needle, the needle retainer arranged to be moved between a retracted position and an extended position.

3. The drive mechanism according to claim 1, wherein each of the first spring and the second spring is arranged as a torsion spring.

4. The drive mechanism according claim 1, further comprising an arrangement for limiting rotation of the first roller relative the second roller.

5. The drive mechanism according to claim 4, wherein one of the first roller or the second roller comprises an internal protrusion adapted engage an arcuate slot within the other one of the first roller or the second roller.

6. The drive mechanism according to claim 4, wherein the first roller is adapted to maintain the needle retainer in a retracted position when the first roller is in the first angular position and to move the needle retainer from the retracted position into an extended position when the first roller is rotated from the first angular position in a second rotational direction to the second angular position.

7. The drive mechanism according to claim 6, wherein the second roller is adapted to rotate the first roller from the second angular position in a first rotational direction to the first angular position through the arrangement for limiting rotation when the second roller is rotated from the third angular position in the first rotational direction to the fourth angular position thereby moving the needle retainer from the extended position into the retracted position.

8. The drive mechanism according to claim 2, further comprising two deflection pulleys, wherein the belt is guided over the deflection pulleys, wherein the belt is fixed to the needle retainer between the two deflection pulleys.

9. The drive mechanism according to claim 1, wherein the trigger mechanism comprises: at least one external recess arranged in either the first roller or the second roller; and at least one trigger hook with a protrusion adapted to engage the at least one external recess for locking either the first roller or the second roller in either the first angular position or the third angular position, respectively.

10. The drive mechanism according to claim 9, further comprising: a trigger button; and an engagement surface on the at least one trigger hook adapted to be engaged by the trigger button upon operation.

11. The drive mechanism according to claim 9, wherein the at least one trigger hook or the trigger button is adapted to be tilted about a respective axis.

12. The drive mechanism according to claim 11, wherein the at least one trigger hook comprises a first trigger hook and a second trigger hook, wherein the protrusion is a first protrusion in the first trigger hook, wherein the second trigger hook comprises a second protrusion, wherein the trigger button is adapted to engage one of the first trigger hook or the second trigger hook thereby disengaging either the first protrusion or the second protrusion, respectively, from the external recess, when the trigger button is tilted in one of the rotational directions, wherein the trigger button is adapted to engage the other one of the first trigger hook or the second trigger hook, thereby disengaging the first protrusion or the second protrusion, respectively, from the external recess, when the trigger button is tilted in the other one of the rotational directions.

13. An insertion arrangement for moving an injection needle between a retracted position and an extended position, the insertion arrangement comprising:

a disposable unit comprising a needle base to which the injection needle is fixed; and a drive mechanism comprising:

a first roller adapted to frictionally engage a belt and rotatably arranged about an axis;

a second roller rotatably arranged about the axis;

a first spring adapted to rotatably bias the first roller against the second roller from a first angular position towards a second angular position;

a second spring adapted to rotatably bias the second roller against an arrester from a third angular position towards a fourth angular position;

the belt adapted to frictionally engage the first roller and adapted to be fixed to a needle retainer; and a trigger mechanism adapted to releasably lock the first roller in the first angular position or the second roller in the third angular position, wherein the needle retainer is adapted to retain the needle base.

14. The insertion arrangement according to claim 13, comprising the needle retainer adapted to retain the injection needle, the needle retainer arranged to be moved between the retracted position and the extended position.

15. The insertion arrangement according to claim 13, wherein each of the first spring and the second spring is arranged as a torsion spring.

16. The insertion arrangement according to claim 13, further comprising an arrangement for limiting rotation of the first roller relative the second roller.

17. The insertion arrangement according to claim 16, wherein one of the first roller or the second roller comprises an internal protrusion adapted engage an arcuate slot within the other one of the first roller or the second roller.

18. The insertion arrangement according to claim 16, wherein the first roller is adapted to maintain the needle retainer in the retracted position when the first roller is in the first angular position and to move the needle retainer from the retracted position into an extended position when the first roller is rotated from the first angular position in a second rotational direction to the second angular position.

19. The insertion arrangement according to claim 18, wherein the second roller is adapted to rotate the first roller from the second angular position in a first rotational direction to the first angular position through the arrangement for limiting rotation when the second roller is rotated from the third angular position in the first rotational direction to the fourth angular position thereby moving the needle retainer from the extended position into the retracted position.

20. An auto-injector comprising:

an insertion arrangement for moving an injection needle between a retracted position and an extended position, the insertion arrangement comprising:

a disposable unit comprising a needle base to which the inaction needle is fixed; and a drive mechanism comprising:

a first roller adapted to frictionally engage a belt and rotatably arranged about an axis;

a second roller rotatably arranged about the axis;

a first spring adapted to rotatably bias the first roller against the second roller from a first angular position towards a second angular position;

a second spring adapted to rotatably bias the second roller against an arrester from a third angular position towards a fourth angular position;

the belt adapted to frictionally engage the first roller and adapted to be fixed to a needle retainer; and a trigger mechanism adapted to releasably lock the first roller in the first angular position or the second roller in the third angular position, wherein the needle retainer is adapted to retain the needle base; and a drug container coupled to the injection needle, the drug container carrying a medicament consisting of at least one pharmaceutically active compound.

\* \* \* \* \*

UNITED STATES PATENT AND TRADEMARK OFFICE
CERTIFICATE OF CORRECTION

PATENT NO. : 10,046,111 B2
APPLICATION NO. : 14/916664
DATED : August 14, 2018
INVENTOR(S) : Schabbach et al.

Page 1 of 1

It is certified that error appears in the above-identified patent and that said Letters Patent is hereby corrected as shown below:

On the Title Page

Item (54), Column 1 (Title), Line 2, delete "ARRANGMENT" and insert -- ARRANGEMENT --, Item (73), Column 1 (Assignee), Line 1, delete "Deutchland" and insert -- Deutschland --, In the Specification In Column 1, Line 2, delete "ARRANGMENT" and insert -- ARRANGEMENT --, In the Claims In Column 11, Line 19, in Claim 4, after "according" insert -- to --, In Column 12, Line 63, in Claim 20, delete "inaction" and insert -- injection --.

Signed and Sealed this
Fifth Day of March, 2019

Andrei Iancu
*Director of the United States Patent and Trademark Office*